United States Patent [19]
Robinson

[11] Patent Number: 5,962,320
[45] Date of Patent: Oct. 5, 1999

[54] ENGINEERED ANTIGEN PRESENTING CELLS AND METHODS FOR THEIR USE

[75] Inventor: William S. Robinson, Burlingame, Calif.

[73] Assignee: Leland Stanford Junior University, Palo Alto, Calif.

[21] Appl. No.: 08/888,360

[22] Filed: Jul. 3, 1997

Related U.S. Application Data

[63] Continuation-in-part of application No. 08/663,157, filed as application No. PCT/US94/04367, Apr. 20, 1994, Pat. No. 5,738,852, which is a continuation-in-part of application No. 08/049,259, Apr. 20, 1993, abandoned.

[51] Int. Cl.$^6$ .............................. C12N 5/10; A61K 45/05
[52] U.S. Cl. ...................... 435/366; 435/325; 424/93.21
[58] Field of Search ................................... 435/325, 366; 424/93.21

[56] References Cited

U.S. PATENT DOCUMENTS

| | | | |
|---|---|---|---|
| 5,716,826 | 2/1998 | Gruber et al. | 435/320.1 |
| 5,738,852 | 4/1998 | Robinson et al. | 424/199.1 |

OTHER PUBLICATIONS

Townsend et al., Science 259:368–370 (1993).
Chen et al., Cell 71:1093–1102 (1992).
Boussiotis et al., Current Opinion in Immunology 6:797–807 (1994).

*Primary Examiner*—Johnny F. Railey, II
*Attorney, Agent, or Firm*—Pennie & Edmonds LLP

[57] ABSTRACT

Autologous, heterologous or xenogeneic primary cells or cell lines are genetically modified ex vivo to render the cells capable of processing and presenting selected antigens to cells of the immune system of a subject, and to express different HLA molecules for matching to the HLA specificity of the subject. The cells are also modified to express immunoregulatory molecules for directing the immune response of the subject. The cells and cell lines are used in methods to treat infectious diseases or cancer, or to prevent infectious disease by inoculation into a host to activate T cells and induce an antigen-specific immune response, and in assays of the cytolytic activity of a subject's T cells. The cells can also be used to suppress an unwanted immune response of a subject to a selected antigen where the cells lack expression of a costimulation molecule needed for T cell activation.

26 Claims, No Drawings

ENGINEERED ANTIGEN PRESENTING CELLS AND METHODS FOR THEIR USE

CROSS-REFERENCE TO RELATED APPLICATIONS

This application is a continuation-in-part of U.S. patent application Ser. No. 08/663,157 filed Jul. 29, 1996, now U.S. Pat. No. 5,738,852, which is a national phase application under 35 U.S.C. § 371 of PCT/US94/04367, filed Apr. 20, 1994, which is a continuation-in-part application of U.S. Ser. No. 08/049,259, filed Apr. 20, 1993, now abandoned.

INTRODUCTION

The present invention relates to cells engineered to direct the immune response of a subject, and to methods of using such cells for therapy and prevention of infectious disease, for therapy of cancer, for antigen-specific suppression of unwanted immune responses in a subject, and for assays of cytotoxic T cells. More particularly, the invention relates to autologous, heterologous or xenogeneic primary cells or cell lines engineered ex vivo to express HLA molecules, immunoregulatory molecules and selected antigens, rendering the cells capable of presenting those antigens to T cells to activate or suppress the T cells and thus enhance or suppress immune responses to the presented antigens.

BACKGROUND OF THE INVENTION

The immune system protects individuals against disease and infection by viruses, bacteria or other infectious agents. The immune system is able to recognize cells of different individuals, including different allogeneic hosts. Ideally, the immune system functions to eliminate an infectious agent from a mammalian host. Specific immune mechanisms are involved in presenting infection with foreign agents, in resolution of such infections, and in control of cancer cells. Resolution of most virus infections (as well as infection with many other intracellular agents) and elimination of cancer cells is the result of a successful cellular (e.g., $T_h1$ helper T cell and cytotoxic T cell) immune response. The cellular immune response results from activation of certain lymphocytes known as T cells.

However, when the immune response is not adequate, the infection can become chronic and persist for many years or even the life-time of the infected host, and can result in life-threatening disease.

Many traditional vaccines expose the immune system to a foreign antigen such as an antigen of an infectious agent to elicit an antigen-specific immune response. The immune response is often predominantly humoral, in which the presence of a foreign antigen elicits the production of antibodies specific for the antigen. For example, an infectious agent antigen may elicit the production of antibodies which neutralize the infectivity of the infectious agent or toxin produced by the agent. Examples include polio and hepatitis A and B, measles, Varicella-zoster, parvovirus and rabies virus antigens. Toxic antigens produced by infectious agents include tetanus toxin, botulinum toxin, diphtheria toxin and pertussis toxin. (See *Fundamental Virology,* Fields et al. eds., 3rd ed., Lippincott-Raven, New York, 1996; and *Microbiology,* Davis et al. eds., 4th ed., Lippincott, New York, 1990). This is in contrast to a cellular response, e.g. by activated T cells.

Current methods of treatment of chronic virus infections often provide little clinical benefit because they frequently fail to terminate the infection. Such treatments include administration of small chemical compounds, such as nucleoside analogs, or biologically active proteins, such as interferons. For example, interferons suppress hepatitis B virus (HBV) and hepatitis C virus (HCV) during treatment of chronic infection but virus usually returns to pretreatment levels when treatment is stopped. These treatments inhibit virus replication but do not eliminate virus from cells, or virus infected cells from the infected host, and may result in limited disease improvement only during their administration. Effective vaccination seeks to prevent infection or modify disease resulting from infection caused by the infectious agent to which the vaccine is directed.

Cancer is also a result of failure of the cellular immune system of a patient to eliminate the offending cells, e.g. cancer cells. The cellular immune response plays a major role in the elimination of murine tumors (Wunderlich et al., *Principles of Tumor Immunity,* In: DeVita et al. (eds.), *Biologic Therapy of Cancer,* Philadelphia, J.B. Lippincott Co., pp. 3–21, 1991) as it does with infecting viruses. Tumor infiltrating lymphocytes (TILs) that recognize unique cancer antigens in an MHC-restricted fashion have been identified in patients with melanoma. (Rosenberg, *J. Clin. Oncol.* 10:180–199 (1993)). Most approaches for immunizing patients with cancer have been directed at stimulating strong T cell immune reactions against tumor associated antigens. These studies indicate that adoptive transfer of T lymphocytes from immune animals can transfer resistance to tumor challenge, and in some cases, result in the elimination of established cancer.

A key attribute of the immune system is its ability to discriminate between self and non-self ("foreign"). Optimally, the mammalian immune system is non-reactive ("tolerant") to self-antigens. The mechanisms that provide tolerance eliminate or render inactive clones of B and T cells that would otherwise carry out anti-self reactions. Autoimmune diseases such as multiple sclerosis, rheumatoid arthritis, lupus erythematosus, and Type 2 diabetes mellitus represent an aberrant immune attack in which antibodies or T cells of a host are directed against self-antigen not normally the target of the immune response. Autoimmunity results from the dysfunction of normal mechanisms of self-tolerance that prevent the production of functional self-reactive clones of B and T cells. Attempts to treat such diseases by suppression of the immune response to date have used methods of immunosuppression that are not antigen specific and cause undesirable side effects such as broad suppression of immune responses including those needed for protection against infectious diseases.

In transplant rejection, certain HLA class I protein products ("transplantation antigens") (HLA-A, B and C) of the donor tissue are recognized by antibodies and/or T cells. In allergic responses IgE is produced in response to activation of $T_h2$ lymphocytes by antigenic substances or "allergens." Treatments for these reactions have generally involved non-antigen specific suppression of the immune response. More recently new approaches such as use of allergen-specific IgG blocking antibodies for competing with IgE antibodies, and activation of antigen-specific suppressor T cells for inducing anergy in $T_h2$ lymphocytes have been investigated.

Methods of antigen specific immune suppression directed at the response to the antigens involved in autoimmune disease ("autoantigens"), transplant rejection and allergic responses are preferred therapeutic approaches to treating these immune disorders.

The mammalian immune system includes B cells and different classes of T cells. CD8+ T (commonly cytotoxic T)

cells recognize antigen peptide plus MHC class I complex. Appropriate T cell activation can result in antigen-specific cytotoxic T lymphocytes (CTLs) able to kill target cells expressing the specific viral or cancer antigens.

CD4+ (predominantly helper) T cells recognize antigen peptide plus MHC class II complex. CD4+ T helper cells are classified into two distinct subsets, the $T_h1$ and $T_h2$ cells, based on their function and pattern of lymphokine secretion. $T_h1$ cells secrete principally IL-2, IL-12, IFNγ and TNF (providing help for the activation of CTLs and an anti-viral or anti-tumor response), while $T_h2$ cells principally secrete IL-4, IL-S, IL-6 and IL-10 (providing help for the humoral immune response, such as antigen specific B cell proliferation, differentiation and maturation). The $T_h1$ type cytokines enhance cellular immunity and have anti-viral or anti-tumor activity. The $T_h2$ type cytokines enhance antibody production, particularly IgE production leading to stimulation of allergic responses, and help respond to extracellular infections.

The differentiation of the CD4+ cells into $T_h1$ or $T_h2$ subsets during the activation process can be influenced not only by the antigenic stimulus but also by the presence of cytokines. Thus, the $T_h1$ or $T_h2$ response can be influenced by exposure to molecules such as cytokines that favor one type of response over the other. Factors that are known to enhance the $T_h1$ response include intracellular pathogens, exposure to IFN, IL-12 and IL-2, the presence of professional APCs and sustained exposure to low doses of antigen. Factors that are known to enhance the $T_h2$ response include exposure to IL-4 and IL-10, APC activity on the part of B lymphocytes and high doses of antigen.

T lymphocytes ("T cells") of the mammalian immune system recognize antigen in the form of short peptides derived ("processed") from the native protein antigen complexed with self glycoproteins encoded by the major histocompatibility complex ("MHC") molecules and transported to the surface of an antigen presenting cell (APC) (Whitton et al. in *Virology*, 2nd Ed., (Fields et al., eds.), Ch. 15, pp. 369–381, Raven Press, Ltd., New York, 1990). MHC recognition of foreign peptides provide antigen specificity for immune responses. The MHC is a cluster of closely linked genetic loci encoding three different classes of polypeptide products (class I, II and III) involved in the generation and regulation of immune responses. Genes encoding MHC polypeptides are present in all vertebrates. Class I and II MHC genes encode cell-surface proteins involved in the presentation of protein antigens to T cells during generation of an immune response. Antigenic peptide fragments of foreign protein antigens complexed with Class I molecules on the surface of antigen presenting cells can be recognized by T cells. Antigen peptide complexed with MHC on the cell surface renders that cell a target for antigen specific cytotoxic T cells. Some tumor associated protein antigens also bind to Class I molecules on the surfaces of neoplastically transformed cells rendering them targets for antigen specific CTLs. In transplant rejection, foreign class I alleles are recognized by the cytotoxic T cell receptor leading to alloreactivity and lysis.

Class II MHC molecules are primarily expressed on the surfaces of B lymphocytes and antigen-presenting macrophages and on activated T cells and are involved in presenting antigen to helper T cells for generating an immune response. In particular, Class II molecules regulate the activation of antigen-specific MHC-restricted helper T cells required for activation of cytotoxic T lymphocytes and antibody-producing B cells. Normally, class II MHC expression is limited to professional antigen presenting cells such as B lymphocytes, macrophages, dendritic cells and activated T cells in humans that process antigens for T cell activation. In humans, there are at least three types of Class II molecules, HLA-DR, DQ and DP.

The human MHC located on chromosome 6 is referred to as HLA (Human Leukocyte Antigen). The combination of molecular alleles at the clustered HLA loci defines the tissue type ("HLA specificity") of an individual. There are vast polymorphisms in each HLA gene locus and each individual has a personal set of Class I and Class II HLA molecules ("self" HLA). HLA molecules serve an important role in human immune system recognition of "self" from "non-self" or foreign. When cells from a donor are introduced into hosts with different HLA genotypes, the donor cells are recognized as foreign for the donor cell HLA molecules and the donor cells are destroyed by the host immune system.

Another important feature of the antigen specific T cell activation is its MHC restriction. T cells from a donor can only be activated by an antigen in complex with "self" MHC (HLA in human) molecules and the activated CTLs can only kill target cells presenting the same antigen in complex with "self" MHC molecules. Activation of T lymphocytes ("T cells") occurs when the T cell receptor (TCR) binds to an antigen peptide complexed with a self HLA molecule on the surface of APCs.

Activation requires not only recognition of the antigen peptide-MHC complex by the TCR (first signal), but also the interaction of costimulation molecules on the surface of APCs with specific molecules on the surface of T cells (second signal) (Freeman et al., *J. Exp. Med.* 174:625–691 (1991)). Such costimulation molecules include B7- 1, B7-2 and B7-3 proteins as well as CD40 (Clark, et. al., *Ann. Rev. Immunol.* 9 97–127 (1991)). In contrast, antigen presentation to T cells in the absence of a second signal, such as the B7-CD28 signal, leads to T cell anergy (tolerance) to the antigen. (Boussiotis et al., *Immunol. Revs.* 153:5–26 (1996); Judge et al., *Immunologic Res.* 15(1):38–49 (1996); McIntosh et al., *Cellular Immunol.* 166(1):103–112 (1995); Boussiotis et al., *Current Op. in Immunol.* 6(5):797–807 (1994); and Gimmi et al., *Proc. Natl. Acad. Sci. USA* 90(14) :6586–6590 (1993)). Antigen-specific tolerance provides a preferred immunosuppressive approach for treatment of auto-immune disease, transplant rejection and allergic reactions.

The level of MHC molecule expression on the cell surface is also an important factor for both the activation and the effector function of T cells. The level of expression of HLA molecules on the cell surface is thought to be regulated by a number of factors. IFN, a lymphokine, can up-regulate the cell surface expression of HLA molecules, enhancing the function of APCs to activate T cells (Revel, et. al., *Trends Biochem Sci* 11 166 (1986)). Other molecules, such as PA28 (Groettrup, et. al., *Nature,* 381:166–8 (1996)), can up-regulate the surface expression of HLA molecules and the loading of antigenic peptides to the HLA molecules.

Two pathways are thought to exist within vertebrate cells to generate peptides for recognition by T cells. One is the endogenous pathway, which processes endogenously expressed antigenic proteins and provides peptides to MHC class I molecules for antigen presentation to CD8+ T cells. This process involves proteasomes and the ubiquitin pathway of protein degradation. Additionally, specific peptide transporter proteins (TAP) transport the peptides across the membrane of the endoplasmic reticulum (ER) to access the lumen, where antigenic peptide is bound to the class I molecule. A large family of related transporter proteins is known as the "ABC (ATP binding cassette) transporters". TAP transporter is a member of this family. The TAP molecule is composed of two polypeptide chains, TAP1 and TAP2, both of which are encoded by genes in the HLA family. The other is the exogenous pathway, which processes exogenous antigenic proteins and provides peptides to HLA Class II molecules for presentation to CD4+ T cells. Peptide loading to HLA class II molecules requires the presence of a molecule, HLA-DM in humans. The class II locus of the HLA genes contains genes encoding proteins involved in antigen processing including LMP2 and LMP7 (genes for two proteasome subunits) and TAP1 and TAP2, peptide transporter heterodimers, and the HLA-DM molecule (DMA and DMB) (Monaco, *J. Leukoc. Biol.* 57:543–547 (1995); Howard, *Curr. Opin. Immunol.* 7:69–76 (1995)). Sufficient cellular levels of expression of such molecules as the peptide transporters and proteasome components are required for cells to present antigen to T cells. The level of expression of HLA molecules is also important for this function.

In recent years, APCs have been contemplated for use as immunogen for cellular therapeutics. There have been a variety of suggestions for modifying cells to provide immunotherapeutics (for review see Tykocinski et al., *Amer. J. Pathol.* 148:1–16 (1996)). Tumor cells have been designed for use in cellular cancer vaccines, for example by introducing genes encoding proteins with known immunostimulatory properties such as cytokines, chemokines, heat shock proteins and MHC molecules into the tumor cells ex vivo (Ostrand-Rosenberg, *Curr. Opin. Immunol.* 6:722–727 (1994); Pardoll, *Curr. Opin. Immunol.* 4:619–623 (1992), Townsend et al., *Science* 259:368–370 (1993); and Townsend and Allison, *Cancer Res.* 54:6477–6483 (1994)). However, gene transfer into tumor cells has limitations because most primary tumor cells grow poorly in cell culture and are poor transfection targets.

Several different cell types can function as professional APCs ("PAPCs"), including macrophages, monocytes, dendritic cells, Langerhans cells and activated B cells. These cells express molecules such as costimulatory molecules capable of providing the second signal for T cell activation. Other cells types (non-professional antigen presenting cells), to varying extents, possess antigen processing and antigen presenting capabilities.

While APCs have been obtained from human hosts for manipulation ex vivo and reintroduction into the host ("autologous APCs"), there remains a need for antigen presenting cells that can be used therapeutically to more strongly stimulate antigen specific immune responses or produce antigen-specific suppression of immune responses. Viral antigens can be degraded in infected cells and specific viral antigen peptide fragments presented at the cell surface complexed with MHC molecules where they serve as targets for MHC-restricted CTLs. However, most virus infected cells in the host can not serve as APCs for the activation of T cells because they do not express molecules that can provide a costimulation signal required for T cell activation. When antigen specific T cell activation is inadequate and fails to eliminate the agent, infections may persist and become chronic. Similarly, most cancer cells can serve only as target cells for CTLs, not as professional APCs for activation of T cells. Cancer results when the cancer-specific T cell activation is not sufficient and CTLs fail to adequately kill cancer cells.

There is thus a need for engineered cells having a compatible HLA specificity to that of a subject, so that the cells can be introduced into the subject to present selected antigens and direct the subject's immune response to these antigens for treatment of infectious diseases and cancer, and for antigen-specific immunosupression of unwanted immune responses.

SUMMARY OF THE INVENTION

The present invention provides cells engineered ex vivo to function as antigen presenting cells in vivo. The engineered cells express specific HLA molecules, one or more selected antigens, and one or more immunoregulatory molecules. The cells include autologous, heterologous and xenogeneic PAPCs, and primary cells that are not PAPCs, as well as cell lines, engineered by introducing immunoregulatory genes and selected antigens, to function as antigen presenting cells.

The selected antigens include antigens such as cancer antigens and antigens of infectious agents or antigens associated with immune responses such as transplant rejection, autoimmunity disease and allergic responses.

The invention provides methods of using these engineered cells and cell lines in vivo in vertebrates, such as humans or animals, to direct the immune response to the selected antigens. In particular, the cells may be used to enhance or suppress the immune response of the subject to the selected antigens. The cells may be engineered to express immunoregulatory molecules that favor $T_h1$ or $T_h2$ responses to the selected antigen to drive the immune response in the desired direction for responding to the selected antigens.

The methods of the invention use the engineered cells expressing class I and class II HLA molecules which are selected to match the HLA specificity of the subject to be treated by introduction of the cells into the subject. The engineered cells also express one or more selected antigens to which the desired immune response or immune suppression is to be directed.

Vertebrate cell lines are modified ex vivo to function as APC lines ("engineered APC lines" or "e-APC lines") by introducing genes encoding different HLA class I and class II molecules, and a selected antigen. The cells may be further engineered to express one or more genes encoding costimulation molecules, ABC transporter proteins, and chemokines. Selected e-APC lines are further modified to express immunoregulatory molecules to enhance the immune response of a recipient subject. e-APC lines are also prepared which lack expression of molecules, such as costimulation molecules, involved in activation of T cells to suppress the immune response.

The invention includes methods of using the e-APC lines to direct the immune response of a subject to a selected antigen such as an antigen of an infectious agent or cancer for therapy of the infectious disease or cancer, or for prevention of infection. The methods include inoculation of an infected or cancer-bearing subject with cells of an e-APC line expressing HLA matching the specificity of the subject to be treated and expressing selected antigens of the cancer or infectious agent present in the subject, or inoculation of an uninfected subject to protect against new infection.

The invention includes methods of using the established e-APC lines to suppress the immune response of a subject to selected antigens where the cells are engineered to present the selected antigens without expression of molecules, such as costimulatory molecules, that provide secondary signals for T cell activation, in order to induce tolerance to the introduced selected antigens.

The methods of the invention also use the cells and cell lines of the invention to selectively enhance or suppress activation of one subset of T lymphocytes, e.g. $T_h1$ or $T_h2$, relative to the activation of another subset of T lymphocytes, to direct the immune response of a subject to the selected antigens.

The invention also includes methods of using the e-APC lines as target cells in an assay of cytotoxic T lymphocytes ("CTLs") from a subject, where the CTLs are specific for the selected antigen expressed by the e-APC line.

DETAILED DESCRIPTION OF THE INVENTION

Vertebrate cells are modified or "engineered" to express one or more selected antigens and immunoregulatory molecules, and to present antigen to cells of the immune system of a subject. The engineered cells direct the immune response of the subject to the expressed selected antigens to enhance or suppress the immune response to the antigens.

"Subject" as used herein refers to vertebrate hosts, particularly to mammals, and includes, but is not limited to, primates, including humans, and domestic animals.

"Selected antigens" as used herein refers to antigens of infectious agents or cancer, or to antigens associated with unwanted immune responses such as autoimmune diseases, transplant rejection and allergic reactions.

"Immunoregulatory molecules" as used herein refers to any molecule occurring naturally in vertebrates that may regulate or directly influence immune responses including proteins involved in antigen processing and presentation such as TAP1/TAP2 transporter proteins, proteosome molecules such as LMP2 and LMP7, and MHC or HLA molecules; factors that provide co-stimulation signals for T cell activation such as B7 molecules and CD40; chemokines; lymphokines and cytokines such as interferons $\alpha$, $\beta$ and $\gamma$, interleukins (e.g., IL-2, IL-12, etc.), factors stimulating cell growth (e.g., GM-CSF,), and other factors (e.g., tumor necrosis factors or TNF).

In one embodiment of the invention autologous PAPCs are taken from a human or animal subject and modified ex vivo to express one or more selected antigens and immunoregulatory molecules, such as lymphokines. The cells may be modified to express selected antigens by introduction of genetic material encoding the selected antigens, or the antigens can be added to or "loaded" on the cells in culture. The modified, autologous PAPCs are then reintroduced into the same subject to enhance the immune response to the expressed antigens. The immunoregulatory molecules can be selected to direct the response of a subset of T lymphocytes, for example, a $T_h1$ or $T_h2$ response.

Alternatively, the autologous PAPCs may be modified to express one or more selected antigens and to lack expression of other molecules, such as costimulation molecules, which mediate a second signal required for activation of T cells. Examples of such molecules needed for T cell activation include B7 molecules or CD40. These molecules interact with ligands such as CD28 on T cells resulting in T cell activation. These cells present selected antigens, but lack expression of molecules for activation of T cells, and can thus induce tolerance or anergy to the selected antigens. The cells can be used for antigen-specific suppression of unwanted immune responses for treatment of autoimmune diseases, transplant rejection and allergic reactions.

In another embodiment of this invention, non-autologous or "heterologous" PAPCs from a donor individual of the same species as the subject that will receive the modified cells, or "xenogeneic" professional APCs (cells from another vertebrate species) are modified ex vivo by genetic engineering to express HLA class I and class II molecules matching the HLA specificity of the subject to be treated. The APCs are also modified to express one or more selected antigens, and may be modified to express one or more immunoregulatory molecules for enhancing the immune response to the antigens. Introduction of HLA antigens matching those of the subject to be treated into heterologous or xenogeneic PAPCs is necessary to render the APCs capable of activating T cells and directing an antigen-specific immune response in that subject.

These cells may be used to enhance the immune response of the subject to selected antigens such as cancer or infectious agent antigens, or to suppress an unwanted immune response. In the latter application, the cells are engineered to express the selected antigens, but not to express molecules needed for activation of T cells, e.g. costimulation molecules.

In another embodiment of the invention autologous, heterologous or xenogeneic vertebrate cells that are not professional APCs are modified ex vivo by genetic engineering to express molecules that enable the cells to function as APCs by presenting antigen to T cells. These molecules include one or more human ABC transporter proteins, chemokines for chemotaxis of T cells, and immunoregulatory molecules, including costimulation molecules such as B7 or CD40, and lymphokines or cytokines such as interleukins, including IL2, IL12, and interferons. The cells also are engineered to express one or more selected antigens. The non-autologous cells are further modified by genetic engineering to express HLA class I and class II molecules with a specificity matching that of the subject to be treated.

These cells may be used to enhance the immune response of the subject to selected antigens such as cancer or infectious agent antigens, or to suppress an unwanted immune response to selected antigens. In the latter application, the cells are engineered to express the selected antigens but not molecules needed for activation of T cells, such as costimulation molecules.

Another embodiment of the invention is APC lines consisting of established vertebrate cell lines that are modified ex vivo express different HLA class I and class II molecules. The cell lines may also be modified to express one or more ABC transporter proteins, such as TAP1 and TAP2 molecules; chemokines for chemotaxis of T cells; and costimulation molecules, such as B7 molecules or CD40. The APC lines are engineered to express one or more selected antigens. The cell lines may also be engineered to express immunoregulatory molecules such as lymphokines or cytokines to direct the immune response. Different HLA class I and class II molecules will be introduced into cell lines to make a plurality of cell lines each with a single different specific HLA type. This creates a "bank" of cells to permit selection of an engineered APC line (e-APC line) which matches the HLA type of a subject to be treated.

These e-APC lines may be used to enhance the immune response of the subject to selected antigens such as cancer or infectious agent antigens, or to suppress the immune response to selected antigens. In the latter application, the APC lines are engineered to express the selected antigens but not molecules needed for activation of T cells, such as costimulation molecules.

In these embodiments the cells and cell lines are engineered by introducing the appropriate genes encoding the selected antigens and functional molecules into the cells ex vivo, or by loading the protein or peptide antigens onto the cells in culture, or by fusing with cells expressing the selected antigens, as described in detail infra.

The invention also includes a method of administering or inoculating therapeutically effective amounts of e-PAPCs, e-APCs or e-APC lines of the invention into an HLA compatible subject to direct the immune response to the selected antigens. In the case of non-autologous cells, the e-APCs, e-PAPCs or e-APC lines are selected to match the HLA specificity of the subject to whom the cells are administered. Such immunization can be used for therapy of infectious diseases, cancer, or for protective vaccination to prevent new infection in uninfected subjects, by enhancing the immune response. Alternatively, a subject can be treated by the methods of the invention to suppress the immune response to selected antigens where desired to treat disorders including autoimmune diseases, transplant rejection and allergy.

The introduced cells will express both the subject's HLA specificity and one or more selected antigens in amounts effective to enhance or suppress an immune response to the antigens.

The e-APCs may be activated ex vivo prior to administration to the subject for more efficient antigen presentation and T cell activation (see T cell activation reviewed by Weiss, A., in "Fundamental Immunology", ed. W. E. Paul, Raven Press, New York, 3rd edition, pp.467–504, 1993).

The cell lines engineered to function as antigen presenting cells (e-APC lines) can also be used as target cells in a method of assaying cytotoxic T cell activity against the selected antigens in T cells recovered from a subject having the same HLA specificity as the e-APC line, as described infra. This information may be used to evaluate immune responses to natural infection or cancer, or after experimental immunization.

5.1 Isolation of Cells

Professional antigen presenting cells ("PAPCs") for use in the invention include any vertebrate cell that functions physiologically to present antigen to T cells and cause T cell activation including, but not limited to, macrophages, B cells, monocytes, dendritic cells, and Langerhans cells.

Cells for use in the present invention also include cells that are not professional APCs, including cells of any vertebrate species, whether or not they are known to function as professional APCs, such as activated T cells, fibroblasts, eosinophils, keratinocytes, astrocytes, microglial cells, thymic cortical epithelial cells, endothelial cells, Schwann cells, retinal pigment epithelial cells, myoblasts, vascular smooth muscle cells, chondrocytes, enterocytes, thyrocytes and kidney tubule cells. These may be primary cells recently explanted from a host and not extensively passaged in cell culture to form an established cell line, or established cell lines that are relatively homogeneous and capable of proliferating for many generations or indefinitely.

PAPCs are collected from the blood or tissue of 1) an autologous donor; 2) a heterologous donor having a different HLA specificity then the host to be treated; or 3) from a xenogeneic donor of a different species using standard procedures (Coligan, et. al., *Current Protocols in Immunology,* sections 3 and 14 (1994)). The cells may be isolated from a normal host or a patient having an infectious disease, cancer, autoimmune disease, or allergy.

For example, PAPCs may be obtained from the peripheral blood using leukopheresis and "FICOLL/HYPAQUE" density gradient centrifugation (stepwise centrifugation through Ficoll and discontinuous Percoll density gradients). Procedures are utilized which avoid the exposure of the PAPCs to antigens which could be internalized by the PAPCs, leading to activation of T cells not specific for the antigens of interest.

Cells that are not professional APCs are isolated from any tissue of 1) an autologous donor; 2) a heterologous donor or 3) a xenogeneic donor, where they reside using a variety of known separation methods (Darling, *Animal Cells: Culture and Media.* J. Wiley, New York, 1994; Freshney, *Culture of Animal Cells.* Alan R. Liss, Inc., New York, 1987).

Non-autologous cells, e.g. heterologous or xenogeneic cells, are engineered ex vivo to express HLA class I and class II molecules that match known human HLA specificities. These cells can then be introduced into a human subject matching the HLA specificity of the engineered cells. The cells are further engineered ex vivo to express one or more selected antigens.

The engineered cells are maintained in cell culture by standard cell culture methods (Darling, *Animal Cells: Culture and Media".* J. Wiley, New York, 1994; Freshney, *Culture of Animal Cells".* Alan R. Liss, Inc., New York, 1987).

Cell lines for use in the present invention are obtained from a variety of sources (e.g., ATCC Catalogue of Cell Lines & Hybidomas, American Type Culture Collection, 8th edition, 1995), or are produced using standard methods (Freshney, *Culture of Immortalized Cells,* Wiley-Liss, New York, 1996). Non-transformed cell lines are preferred for use in human subjects.

5.2 Selected Antigens

Selected antigens to be expressed by the e-APCs, e-PAPCs and e-APC lines of the invention consist of one or more selected antigens or epitopes of an infectious agent or cancer, or of a transplantation antigen, allergen or autoantigen.

Antigens or epitopes of an infectious agent include, but are not limited to, antigens or proteins encoded by the genomes of: Hepadnaviridae including hepatitis B virus (HBV); Flaviviridae including human hepatitis C virus (HCV), yellow fever virus and dengue viruses; Retroviridae including human immunodeficiency viruses (HIV) and human T lymphotropic viruses (HTLV1 and HTLV2); Herpesviridae including herpes simplex viruses (HSV-1 and HSV-2), Epstein Barr virus (EBV), cytomegalovirus (CMV), varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B-19; Arenaviridae including Lassa virus; Orthomyxoviridae including influenza viruses; Poxviridae including Orf virus, molluscum contageosum virus and Monkey pox virus; Togaviridae; Coronaviridae including corona viruses; and Picornaviridae.

Particularly suitable infectious agent antigens are those which induce a T cell response, and particularly a CTL-response during infection. These may include, for example, from HBV, the core antigen, the E antigen and the surface antigen (HBsAg)(Okamoto et al., *J. Gen. Virol.* 67:1383–1389 (1986) (HBsAg from HBV)).

Non-viral organisms that are controlled by T cell immune responses include: pathogenic protozoa (e.g. Pneumocystis carinii, Trypanosoma, Leishmania, Plasmodia, and Toxoplasma gondii); bacteria (e.g., Mycobacteria, and Legioniella) and fungi (e.g. Histoplasma capsulatum and Cocidioides immitus).

These antigens are targets for therapy and/or prevention by the cell therapy strategy described herein.

Cancer antigens for use in the invention include, but are not limited to, melanoma tumor antigens (Kawakami et al., Proc. Natl. Acad. Sci. USA 91:3515–3519 (1994); Kawakami et al., *J. Exp. Med.,* 180:347–352 (1994); Kawakami et al. *Cancer Res.* 54:3124–3126 (1994), including MART-1 (Coulie et al., *J. Exp. Med.* 180:35–42 (1991), gp100 (Wick et al., *J. Cutan. Pathol.* 4:201–207 (1988) and MAGE antigen, MAGE-1, MAGE-2 and MAGE-3 (Van der Bruggen et al., *Science,* 254:1643–1647 (1991)); CEA, TRP-1, P-15 and tyrosinase (Brichard et al., *J. Exp. Med.* 178:489 (1993)); HER-2/neu gene product (U.S. Pat. No. 4,968,603); estrogen receptor, milk fat globulin, p53 tumor suppressor protein (Levine, *Ann. Rev. Biochem.* 62:623 (1993)); mucin antigens (*Taylor-Papdimitriou,* International Pub. No. WO90/05142)); telomerases; nuclear matrix proteins; prostatic acid phosphatase; papilloma virus antigens; and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (e. g., Rosenberg, *Ann. Rev. Med.* 47:481–91 (1996).

Autoantigens for use as selected antigens include, but are not limited to, myelin basic protein; islet cell antigens; insulin; collagen and human collagen glycoprotein 39.

Transplantation antigens for use as selected antigens include, but are not limited to, different antigenic specificities of HLA-A, B and C Class I proteins. Different antigenic specificities of HLA-DR, HLA-DQ, HLA-DP and HLA-DW Class II proteins will also be used (*WHO Nomenclature Committee, Immunogenetics* 16:135 (1992); Hensen et al., in *"Fundamental Immunology,"* ed. W. Paul, pp. 577–628, Raven Press, New York, 1993; and see NIH Genbank and EMBL data bases for HLA protein sequences).

Allergen antigens include, but are not limited to, environmental allergens such as dust mite allergens; plant allergens such as pollen, including ragweed pollen; insect allergens such as bee and ant venom; and animal allergens such as cat allergens.

5.3 Methods for Engineering Cells

The practice of the present invention employs conventional techniques of molecular biology, microbiology, recombinant DNA and immunology, within the skill of these arts. Such techniques are found in the scientific literature. (See, e.g., Brock, *Biology of Microorganisms,* Eighth Ed., (1997), (Madigan et al., eds.), Prentice Hall, Upper Saddle River, N.J.; Sambrook et al., *Molecular Cloning: A Laboratory Manual,* Second Ed., (1989); Oligonucleotide Synthesis, M. J. Gait Ed., 1984, *Animal Cell Culture,* Freshney, ed., 1987; *Methods In Enzymology,* series, Academic Press, Inc.; *Gene Transfer Vectors for Mammalian Cells,* Miller and Calos, Eds., 1987; *Handbook of Experimental Immunology,* Weir and Blackwell, Eds., *Current Protocols in Molecular Biology,* Ausubel et al., Eds., 1987. and *Current Protocols in Immunology,* Coligan et al., Eds., 1991)). These references are incorporated in their entirety herein by reference.

The methods described below to modify cells are merely for purposes of illustration and are typical of those that might be used. However, other procedures may also be employed to obtain expression of selected molecules in cells, as is understood in the art.

5.3.1 Gene Transfer

5.3.1. (a) Genes

In accordance with the invention, e-APCs, e-PAPCs and e-APC lines expressing one or more selected antigens, capable of stimulating [or suppressing an immune response, and expressing additional selected molecules, including immunoregulatory molecules, are produced ex vivo by the insertion of one or more recombinant or synthetic nucleic acid sequences (genes) encoding these molecules, or functional domains thereof, such that the molecules are expressed in effective amounts in the recipient host cell. By "effective amount" is meant that expression is sufficient to enable the recipient cell to provoke the desired immune response in vivo.

Nucleotide sequences encoding selected antigens, ABC transporter proteins, immunoregulatory molecules including costimulation molecules, lymphokines, and chemokines, and the functional domains of these molecules, are known, and/or obtainable using methods known in the art.

For example, the ABC transporter proteins, human TAP1 and TAP2, have been cloned as disclosed in Trowsdale et al., *Nature* 348:741 (1990); and Powis et al., *Immunogenetics* 37:373 (1993). Additional molecules involved in antigen processing and presentation include invariant chain Ii-cs (Miller et al., *Cell* 74:257 (1993); Vidal, *J. Immunol* 151:4642 (1993)).

DNA sequences encoding lymphokines include, but are not limited to: interleukins including IL-2 (Taniguchi et al., *Nature,* 302:305 (1983); Devos et al., *Nucl. Acid. Res.* 11:4307–23 (1983)), IL-1 (Gubler et al., *J. Immunol.* 136:2492–97 (1986); Bensi et al., *Gene* 52:95–101 (1987) and Nishida et al., *Biochem. Biophys. Res. Comm.* 143:345–352 (1987)),and IL-12 (Wolf et al., *J. Immunol.* 146:3074–3081 (1991)); GM-CSF (Ladner et al., EMBO J. 6:2693–98 (1987); TNF (Shirai et al., *Nature* 313:803–806 (1985); and Wang, *Science* 228:149–154 (1985)); and interferons ("IFN") including IFNα (Streuli et al., *Science* 209:1343–47 (1980) and Henco et al, *J. Mol. Biol.* 185:227–260 (1985)), IFNβ (Goeddel et al., *Nucl. Acid. Res.* 8:57–74 (1980)) and IFNγ (Nishi et al., *J. Biochem.* 97:153–159 (1985); Gray and Goeddel, *Nature* 298:859–863 (1982)) (coding sequences of these and other lymphokines are found in the EMBL and NIH Genbank data bases and See Webb and Goeddel, eds., *Lymphokines, Vol. 13: Molecular Cloning and Analysis of Lymphokines,* Academic Press, New York, 1982)).

DNA sequences encoding costimulation molecules are known and include, but are not limited to, B7-1 (Freeman et al., *J. Immunol.* 143:2714–2722 (1989); B7-2 (Azuma et al., *Nature* 366:76–79 (1993) and B7-3 molecules; 4.1 BB ligand (Goodwin et al., *European J. Immunol.* 23:2631 (1993); Alderson et al., *Europ. J. Immunol.* 24:2219 (1994)); ICAM-1 (Simmons et al., *Nature* 331:624–627 (1988); Swain, *J. Immunol.* 155:45 (1995); Damle, *J. Immunol.* 151:2368 (1993)), LFA-3 (Wallner et al., *J. Exp. Med.* 166:923–932 (1987); Seed et al., *Nature* 329:840–842 (1987)), CD72 (NIH Genbank, Yng et al., *J. Immunol.* 154:2743 (1995) (murine CD72); and see *Molecular Immunology,* 2nd edition, ed. Hames and Glover, IRL Press, New York, p. 263)); CD40 (Shamadzu et al., *Biochim. Biophys. Acta* 126:67–72 (1995) and heat-stable antigen (hsa) (Liu, J. Exp. Med. 175:437–445 (1992)).

DNA sequences encoding chemokines such as MCP-1 (Yoshimura, et. al., FEBS Lett. 244 487–93 1989; Rollins, et. al., *Mol. Cell Biol.* 9 4687–95, 1989) and RANTES (Schall, et. al., *J. Immunol.* 141 1018–25, 1988; and Nelson, et. al., *J. Immunol.* 151 2601–12, 1993) and others are published and are found in the EMBL and NIH Genbank data bases.

DNA sequences encoding HLA molecules of different HLA types (coding sequences of known HLA molecules are found in the EMBL and NIH Genbank data bases) are introduced into non-autologous e-APCs and APC lines.

DNA encoding allergens include cDNAs encoding the dust mite allergens Der pI and Der pII (Chua et al., J. Exp. Med. 167:175–182 (1988); Chua et al., Int. Arch. Allergy Appl. Immunol. 91:124–129 (1990)); ragweed pollen antigen Amb a1 (Rafnar et al., J. Biol. Chem. 266:1229–1236 (1991); phospholipase $A_2$ bee venom allergen (Dhillon et al., J. Allergy Clin. Immunol., 89:174, abstract no. 119 (1992)); and the Fel d1 cat allergen (Rogers et al., Mol. Immunol. 30:559–568 (1993)).

All genes of infectious agents encode proteins that are potentially antigenic (foreign antigens) in vertebrate hosts and thus represent possible genes for expression of antigens which would be useful selected antigens for the method described herein. Although many genes of many infectious agents have been cloned and sequenced, others have not. Similarly, many tumor antigen genes, transplantation antigen genes, autoantigen genes, and genes for allergens have been identified and sequenced, others have not. It is intended that other genes identified, isolated and cloned in the future using methods known in the art for molecules having the desired functions (e.g. selected antigen genes and immunoregulatory molecules) will be used in the present invention. All genes capable of functioning as selected antigens in the cells and methods of the present invention are contemplated for use in the cells and methods described herein.

5.3.1(b) Methods of Gene Transfer Into and Expression in Cells

Techniques for nucleic acid manipulation are well known. (See, e.g., Sambrook et al., (1989); Ausubel et al. (1987) and in Annual Reviews of Biochemistry, 61:131–156 (1992)). Reagents useful in applying such techniques, such as restriction enzymes and the like, are widely known in the art and commercially available from a number of vendors.

Large amounts of the nucleic acid sequences encoding the selected molecules for expression in the e-APCs and e-APC lines of the invention may be obtained using known procedures for molecular cloning and replication of the vector or plasmid carrying the sequences in a suitable host cell. DNA sequences encoding a desired protein, for example encoding an infectious agent antigen, can be assembled from cDNA fragments and oligonucleotide linkers, or from a series of oligonucleotides, to provide a synthetic infectious agent gene which can be expressed. Such sequences are preferably provided in the form of an open reading frame uninterrupted by internal nontranslated sequences or introns, which are typically present in eukaryotic genes. Genomic DNA containing the relevant sequences can also be used. Sequences of nontranslated DNA may be present 5' or 3' from the open reading frame, where such sequences do not interfere with manipulation or expression of the coding regions. Either complete gene sequences or partial sequences encoding desired antigenic peptides can be employed.

The nucleic acid sequences for use in the present invention may also be produced in part or in total by chemical synthesis, e.g. by the phosphoramidite method described by Beaucage and Carruthers, Tetra. Letts. 22:1859–1862 (1981), or the triester method (Matteucci et al., J. Am. Chem. Soc. 103:3185 (1981)), and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

The natural or synthetic nucleic acid fragments coding for a desired sequence may be incorporated into vectors capable of introduction into and replication in a prokaryotic or eukaryotic cell. Usually the vectors are suitable for replication in a unicellular host, such as yeast or bacteria, but may also be introduced into cultured mammalian or plant or other eukaryotic cell lines, with and without integration within the genome. The vectors will typically comprise an expression system recognized by the host cell, including the intended recombinant nucleic acid fragment encoding the desired polypeptide. The vectors will also contain a selectable marker, i.e. a gene encoding a protein needed for the survival or growth of a host cell transformed with the vector. The presence of this gene ensures the growth of only those host cells which express the inserted nucleic acid of interest. Typical selection genes encode proteins that 1) confer resistance to antibiotics or other toxic substances, e.g. ampicillin, neomycin, methotrexate, etc.; b) complement auxotrophic deficiencies, or c) supply critical nutrients not available from complex media, e.g. the gene encoding D-alanine racemase for Bacilli. The choice of the proper selectable marker will depend on the host cell, and appropriate markers for different hosts are well known in the art. Such vectors may be prepared by means of standard recombinant techniques well known in the art (Sambrook et al., (1989); Ausubel et al., (1987)).

For gene transfer into the cells to express the selected molecules, nucleic acid may be directly introduced ex vivo in the form of "naked" nucleic acid, e.g. by microinjection, electroporation, as calcium-phosphate-DNA gels, with DEAE dextran, or in encapsulated form, e.g. in vesicles such as liposomes, or in a suitable viral vector.

Vectors containing the nucleic acid encoding the desired molecules for expression in the e-APCs, e-PAPCs and e-APC lines, are preferably recombinant expression vectors in which high levels of gene expression may occur, and which contain appropriate regulatory sequences for transcription and translation of the inserted nucleic acid sequence. Regulatory sequences refers to those sequences normally associated (e.g. within 50 kb) of the coding region of a locus which affect the expression of the gene (including transcription of the gene, and translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosomal entry site (IRES) sequence may be placed between recombinant coding sequences to permit expression of more than one coding sequence with a single promotor.

Transcriptional control regions include: the SV40 early promoter region, the cytomegalovirus (CMV) promoter (human CMV IE94 promoter region (Boshart et al, Cell, 41:521–530 (1985)); the promoter contained in the 3' long terminal repeat of Rous sarcoma virus or other retroviruses; the herpes thymidine kinase promoter; the regulatory sequences of the methallothionein gene; regions from the human IL-2 gene (Fujita et al., Cell, 46:401–407 (1986)); regions from the human IFN gene (Ciccarone et al., J. Immunol. 144:725–730 (1990)); regions from the human IFN gene (Shoemaker et al., Proc. Natl. Acad. Sci. USA 87:9650–9654 (1990)); regions from the human IL-4 gene (Arai et al., J. Immunol. 142:274–282 (1989)); regions from the human lymphotoxin gene (Nedwin et al., Nucl. Acids.

res. 13:6361–6373 (1985)); regions from the human granulocyte-macrophage CSF gene (GM-CSF) (Miyatake et al., EMBO J. 4:2561–2568 (1985)); and others. When viral vectors are employed, recombinant coding sequences may be positioned in the vector so that their expression is regulated by regulatory sequences such as promoters naturally residing in the viral vector.

In addition, operational elements may include leader sequences, termination codons, and other sequences needed or preferred for the appropriate transcription and subsequent translation of the inserted nucleic acid sequences. Secretion signals may also be included whether from a native protein, or from other secreted polypeptides of the same or related species, which permit the molecule to enter cell membranes, and attain a functional conformation.

It will be understood by one skilled in the art that the correct combination of expression control elements will depend on the recipient ("host") cells chosen to express the molecules. The expression vector should contain additional elements needed for the transfer and subsequent replication of the expression vector containing the inserted nucleic acid sequences in the host cells. Examples of such elements include, but are not limited to, origins of replication and selectable markers.

The vector may contain at least one positive marker that enables the selection of cells carrying the inserted nucleic acids. The selectable molecule may be a gene which, upon introduction into the APC, expresses a dominant phenotype permitting positive selection of cells carrying the gene. Genes of this type are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Suitable vectors for the invention may be plasmid or viral vectors, including baculoviruses, adenoviruses, poxviruses, adenoassociated viruses (AAV), and retrovirus vectors (Price et al, *Proc. Natl. Acad. Sci. USA* 84:156–160 (1987) such as the MMLV based replication incompetent vector pMV-7 (Kirschmeier et al., *DNA* 7:219–225 (1988)), as well as human and yeast artificial chromosomes (HACs and YACs). Plasmid expression vectors include plasmids including pBR322, pUC or Bluescript™ (Stratagene, San Diego, Calif.).

Recombinant viral vectors are introduced into e-APC, e-PAPCs and e-APC lines using standard infection conditions. Infection techniques have been developed which use recombinant infectious virus particles for gene delivery into cells. Viral vectors used in this way include vectors derived from simian virus 40 (SV40; Karlsson et al., *Proc. Natl. Acad. Sci. USA* 82:158 (1985)); adenoviruses (Karlsson etl al., EMBO J., 5:2377 (1986)); AAV (Carter, *Current Opinion in Biotechnology*, 3:533–539 (1992)); vaccinia virus (Moss, et. al., *Vaccine*, 6:161–3, 1988)); and retroviruses (Coffin, in Weiss et al., (eds.), *RNA Tumor Viruses*, 2nd ed. Vol. 2, Cold Spring Laboratory, New York, pp. 17–71 (1985)).

In retroviral vectors, genes are inserted so as to be under the transcriptional control of the promoter incorporated in the retroviral long terminal repeat (LTR), or by placing them under the control of a heterologous promoter inserted between the LTRs. This latter strategy provides a way of coexpressing a dominant selectable marker gene in the vector, thus permitting selection of cells that are expressing specific vector sequences.

Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al., cell 33:153 (1983); Miller and Buttimore, *Mol. Cell. Biol.* 6:2895 (1986) (PA317, ATCC CRL9078). Packaging cell lines which contain amphotrophic packaging genes able to transduce cells of human and other species origin are preferred.

DNA vectors containing the inserted genes or coding sequences are introduced into e-APCs, e-PAPCs or e-APC lines using standard methods of transfection such as electroporation, liposomal preparations, Ca-PH-DNA gels, DEAE-dextran, nucleic acid particle "guns" and other suitable methods.

In general, nucleic acid encoding the selected molecules is inserted by standard recombinant DNA methods into a vector containing appropriate transcription and translation control sequences, including initiation sequences operably linked to the gene sequence to result in expression of the recombinant genes in the recipient host. Operably linked refers to a juxtaposition wherein the components are in a relationship permitting them to function in their intended manner. For instance, a promoter is operably linked to a coding sequence if the promoter effects its transcription or expression.

The nucleic acid sequences encoding the proteins or protein fragments selected for expression in e-APCs, e-PAPCs and e-APC lines are inserted in a single vector or in separate vectors. More than one gene encoding a selected antigen, or portion thereof, may be inserted into a single vector or in separate vectors for introduction into the APCs.

Expression of recombinant genes of interest after introduction into APCs is confirmed by immunoassays or biological assays for functional activity of the protein product. For example, expression of introduced molecules into cells may be confirmed by detecting the binding of labeled antibodies specific for the molecules to the cells using assays well known in the art such as FACS (Fluorescent Activated Cell Sorting) or ELISA (enzyme-linked immunoabsorbent assay).

Biological activity of the engineered cells can be verified, for example, in in vitro assays and in animal models such as mice or non-human primates prior to testing in humans. The ability of the engineered cells of the invention to function as desired, e.g. to process and present antigen for enhancing or suppressing an immune response may be tested using in vitro and/or in vivo assays.

CTL lysis of target cells depends on presentation of foreign antigen peptides bound to class I MHC molecules. Thus, efficacy of the APCs of the invention will be determined in part by the ability of the introduced selected antigens to form peptide/MHC complexes on the surface of the e-APCs in vivo. To determine activity of the engineered APCs, the following can be determined: expression of the introduced selected antigen; binding of the antigen or fragment to class I MHC molecules on the APC surface; and stimulation of CTL lysis of host cells bearing the selected antigen. To determine expression of the introduced selected antigen, antibodies which recognize the antigen may be labeled and binding to the e-APCs determined using conventional techniques, such as an ELISA or Western blotting.

To determine if the expressed selected antigen will become bound to the class I MHC (and thus transported to the surface of the e-APC), procedures such as mass spectrometric analysis of transfected APCs may be used. Alternatively, binding to class I MHC molecules can be confirmed using an in vitro antigen-specific T cell activity assay in response to stimulation by MHC antigens, such as described by Coligan et al., "Current Protocols in Immunology, Unit 3.11, Wiley & Sons, 1994.

T cell activation may be detected by various known methods, including measuring changes in the proliferation of T cells, killing of target cells and secretion of certain regulatory factors, such as lymphokines, expression of mRNA of certain immunoregulatory molecules, or a combination of these. The effects of the engineered cells on T cell activation may then be determined using in vitro assays, or by introducing the engineered cells into an animal model, such as a mouse, and subsequently measuring the immune response of the mouse to the selected antigen with controls in which no engineered cells or differently engineered cells were introduced. For example, the e-APCs may be introduced into an animal model, such as a mouse or non-human primate, to determine whether the e-APCs and e-APC lines of the invention can stimulate CTL responses against selected antigens. One such model for determining antigen-specific CTL activity uses mice lacking endogenous active T lymphocytes, such as nude or irradiated mice. Adoptive transfer of selected antigen primed CTLs into such mice in which cells bearing the selected antigen (e.g. cancer cells) have also been introduced permits in vivo assessment of the lytic ability of the transferred CTLs against the introduced cells (see protocols for adoptive transfer, CTL depletion and in vivo T cell activity assays, in Coligan et al., supra at Unit 4.1; and Shastri and Gonsalez, *J. Immunol.* 150:2724–2736 (1993)).

Similarly, selective induction of a $T_h1$ or $T_h2$ immune response, can be determined by, for example, introducing the cells of the invention into an animal model, e.g. a mouse, and measuring the production of specific lymphokines or the expression of their RNAs in spleen cells. In addition, production of IgG 2A antibodies (serological markers for a $T_h1$ response) as compared to production of IgG 1 antibodies (markers for a $T_h2$ response) can be measured using standard methods, such as an ELISA.

Genes to be introduced into such vectors include those encoding selected antigens as described above, selected class I and class II HLA molecules, costimulation and other immunoregulatory molecules, ABC transporter proteins, including the TAP1 and TAP2 proteins, along with appropriate regulatory regions to drive expression of the recombinant coding sequences within recipient host cells. Thus, various combinations of coding sequences may be inserted in a suitable expression vector or vectors.

Sequences encoding selected antigens, costimulation molecules and other immunoregulatory proteins will include at least a portion of the coding sequence sufficient to provide the engineered cell with the desired function. For example, in the case of a costimulation molecule, a portion of the coding sequence that enables it to bind its ligand on T cells can be used. Methods for determining such binding domains of molecules are known in the art. See, for example, Linsley et al., *Proc. Natl. Acad. Sci. USA* 87:5031–5035 (1990). Extracellular domains and transmembrane domains of costimulation molecules, as well as other immunoregulatory molecules, are preferably included.

With respect to the selected antigen, the antigen or antigens expressed in the APCs or cell lines will include portions of the antigen protein sufficient to permit recognition by the cells of the immune system, such as T cells, in the host.

The genes encoding the selected antigen may encode a native protein antigen, a native protein antigen with a separate adjuvant to enhance endocytosis of the protein antigen, a protein antigen conjugated or linked to an adjuvant or adjuvant-like molecule, or a bioengineered chimeric protein consisting of antigen-adjuvant fusion protein.

5.3.1(c) Protein Transfer

As an alternative to gene transfer into cells, protein molecules can be added to e-APCs in culture and "loaded" on the APC for presentation of the molecules to T cells (See, 7Tykocinski et al., *Amer. J. Pathol.* 148:1–16 (1996), incorporated by reference herein). In the case of tumor antigens, tumor cell homogenates can be similarly added to e-APCs in culture to "load" tumor antigens present in the tumor cells. Peptide or protein pulsing (co-culturing) may also be used (Inaba et al., *J. Exp. Med.* 172:631–640 (1990)).

Alternatively, molecules may be introduced to cell surfaces via fusion with liposomes bearing the selected antigen molecules (Coeshott et al., *J. Immunol.* 134:1343–1348 (1985)). Cell fusion techniques include those in which tumor antigen bearing or viral antigen bearing cells are fused with e-APCs to introduce the desired target antigen into the e-APCs (Guo et al., *Science* 263:518–520 (1994)).

5.4 Preparation of Engineered Antigen Presenting Cell Lines

The engineered APC lines of the invention consist of vertebrate cells that can proliferate indefinitely in culture as permanent cell lines. Non-transformed cell lines are preferred. Such cell lines are available commercially (e.g., ATCC Catalogue of Cell Lines & Hybridomas, American Type Culture Collection, 8th edition, 1995) or are created by promoting growth of cells taken from the tissue of a vertebrate using published methods (Freshney, "*Culture of Immortalized Cells*". Wiley-Liss, New York, 1996).

Cells are dissociated from the tissue, for example using an enzyme, and are spread on the bottom of a flat surface, such as a petri dish, where they adhere. A suitable culture medium is added and the culture is incubated. A small amount of blood serum is usually necessary as well as antibiotics to prevent bacterial contamination of the culture.

Vertebrate cells that may be used to form the engineered cell lines of the invention include, but are not limited to fibroblasts, such as WI-38 human diploid fibroblasts, keratinocytes and other cells.

5.5 Pharmaceutical Preparations of Engineered Cells e-APCs, e-PAPCs or e-APC lines of the invention expressing one or more selected antigens or active portions thereof, and HLA antigens having the specificity of the subject to be treated, are grown in cell culture using standard methods (see, e.g. Darling, "*Animal Cells: Culture and Media*". J. Wiley, New York, 1994; and Freshney, "*Culture of Animal Cells*". Alan R. Liss, Inc., New York, 1987). The cells may also express immunoregulatory molecules such as lymphokines.

The engineered cells are suspended in any known physiologically compatible pharmaceutical carrier, such as cell culture medium, physiological saline, phosphate-buffered saline, cell culture medium, or the like, to form a physiologically acceptable, aqueous pharmaceutical composition. Parenteral vehicles include sodium chloride solution, Ringer's dextrose, dextrose and sodium chloride, lactated Ringer's. Other substances may be added as desired such as antimicrobials.

5.6 Introduction of e-APCs into Subjects

Engineered APCs (e-APCs, e-PAPCs or e-APC lines) of the invention expressing the selected antigen and other molecules described herein, are introduced into a subject with an antigen or antigens corresponding to those in the engineered APC to be used, for therapy in amounts sufficient to achieve a therapeutic effect. Alternatively, engineered APCs are introduced into a disease-free subject for protection against infection. A "therapeutically effective amount" of a composition of the invention is a dose sufficient to induce, enhance or suppress an immune response to the selected antigen expressed by the engineered APCs of the invention.

The engineered APCs may be introduced into the subject to be treated by using one of a number of methods of administration of therapeutics known in the art. For example, the engineered cells may be inoculated (with or without adjuvant) parenterally (including, for example, intravenous, intraperitoneal, intramuscular, intradermal, and subcutaneous), by ingestion, or applied to mucosal surfaces. Alternatively, the APCs of the invention are administered locally by direct injection into a cancerous lesion or infected tissue. "Inoculation" refers to administration of the compositions of the invention to a subject.

Routes of administration include epidermal administration including subcutaneous or intradermal injections. Transdermal transmission including iontophoresis may be used, for example "patches" that deliver product continuously over periods of time.

Mucosal administration of the engineered cells of the invention is also contemplated, including intranasal administration with inhalation of aerosol suspensions. Suppositories and topical preparations may also be used.

The methods of the invention contemplate the dosage of a sufficient number of engineered cells to express the selected antigens and immunoregulatory molecules effective to activate or suppress T cells.

The e-APCs of the invention are introduced in at least one dose into an HLA matched subject, with sufficient numbers of e-APCs to activate cells of the immune system and induce an immune response against the infectious agent or cancer antigen. The cells are administered in a single infusion, in a range of at least $10^6$ to $10^{10}$ cells/m$^2$, or in multiple sequential infusions.

Different subjects are expected to vary in responsiveness to such treatment. Dosages will vary depending on such factors as the individual's age, weight, height, sex, general medical condition, previous medical history, disease progression and tumor burden. Therefore, the amount of engineered APCs infused as well as the number and timing of subsequent infusions, is determined by a medical professional carrying out the therapy based on the response of the patient.

After immunization, the efficacy of the cell therapy is assessed by a number of methods, such as assays that measure T cell proliferation, T cell cytotoxicity, antibody production or reduction in the number of antigen positive cells or tissues and/or clinical response. An increase in the production of antibodies or immune cells recognizing the selected antigen will indicate an enhanced immune response. Similarly, an increase in specific lytic activity or specific cytokine production by the subject's immune cells, or tumor regression will indicate efficacy. Efficacy may also be indicated by reduction in the amount or elimination of a virus or other infectious agent, or improvement in or resolution of the disease (pathologic effects), associated with the reduction or disappearance of the unwanted immune response, or improvement in or resolution of the disease (pathologic effects) associated with the unwanted immune response (e.g. autoimmune disease) allergic reaction or transplant rejection).

The therapeutic effects of the invention result from stimulation, or enhancement, or suppression of an antigen-specific immune response by the introduced engineered APCs or cell lines.

Administration of heterologous (different individual) or xenotropic (different species) engineered APCs transfected with and expressing HLA molecules matched to the subject to be treated can provide a stronger immune response than administration of autologous cells. The resulting immune response can provide a therapeutic effect in patients with infection or cancer, or suppress unwanted immune responses.

5.7 Use of e-APC and e-APC Lines for in vitro Assay of CTL Activity

The e-APC lines of the invention are used as target cells in assays to assess the activity of a subject's antigen-specific CTLs.

Cell preparations containing T lymphocytes are recovered from blood or tissue of a patient whose CTL activity is to be assayed. For example, buffy coats consisting of leukocytes are prepared by apheresis from blood samples. "FICOLL HYPAQUE" gradient centrifugation (Boyuwn, Scand. J. Clin. Lab. Invest. 21:21–29 (1968)) followed by four-layer "PERCOLL" (Pharmacia, Uppsala, Sweden) discontinuous centrifugation (Markowicz and Engleman, J. Clin. Invest. 85:955 (1990)) is used. Monocytes are removed from the interface over the "PERCOLL" 50.5% layer, whereas T lymphocytes are collected from the high buoyant density (HD) fraction, or interface between 75% and 50.5% layers. Immune cells including T cells can also be recovered from tissues. The cells may be propagated in cell culture in the presence of the antigen to which an antigen specific CTL response is to be assayed and IL-2.

The T lymphocyte-containing cell preparation is then tested for cytotoxicity against engineered APC target cells expressing the selected antigen to which the CTL response is to be measured and HLA molecules matching the specificity of the host donor of the CTL. Cytotoxic activity can be measured, for example, by $^{51}$Cr release from $^{51}$Cr labeled target cells in a standard CTL assay format. An e-APC cell line prepared according to the methods of the invention and having a matched HLA antigen specificity to the host T lymphocytes is labeled with $^{51}$Cr and used as the target cell for the cytotoxicity assays.

Target cells are incubated with $^{51}$Cr (NEN DuPont, Wilmington, Del.) for 2 hours at 37 C. Excess unlabeled $^{51}$Cr in the supernatant is washed off by sequential centrifugal washing steps in AB Culture Medium. Radiolabeled target cells are suspended in cell culture medium and a number such as 2000 target cells are added to each well of a 96-well microtiter plate. Different numbers of cells of the T cell-containing preparations (effector cells) are added to different wells to make a series of effector cell:target cell ratios of 1:1 to 100:1. Following incubation, the plates are centrifuged to pellet the cells, and aliquots of the supernatant from each well are assayed for $^{51}$Cr in a gamma counter. Controls for spontaneous release of $^{51}$Cr (absence of host immune cells), and for maximal $^{51}$Cr by adding detergent Triton X-100 (Sigma Chemical Co., St. Louis, Mo.) to target cells are carried out in parallel.

The percentage specific release is calculated as

[(experimental release-spontaneous release)/(total release-spontaneous release)]×100

Uses of the Invention

The engineered cells and cell lines described herein which are engineered to function to present antigens can be used in a cell-based therapeutic vaccine to direct the immune response to treat infectious diseases, cancer and unwanted immune responses such as autoimmune disease, transplant rejection and allergic reaction by selecting and using cells expressing HLA antigen matched to the HLA specificity of that of the patient to be treated. The HLA compatibility permits the engineered cells to present antigen that is properly recognized by T cells in the subject into which the cells are introduced. The cells express antigens and molecules selected to enhance or suppress the immune response, and are inoculated in a therapeutically effective number of cells into the patient.

Such cells can be similarly used as a protective cell-based vaccine to induce immunity that prevents new infection in uninfected subjects. The cells express HLA molecules matching those of the host to be immunized and selected antigens.

The engineered cells described herein can also be used as target cells to assay antigen-specific cytotoxic activity of T lymphocytes of an HLA compatible subject.

Advantages of the invention include the fact that non-autologous cells may be used to treat subjects, making a source of cells more readily available. For example, a "bank" of universal e-APC lines may be prepared as described herein consisting of a plurality of different cell lines each expressing a different HLA type, including the most common HLA types. In addition, cell lines expressing each HLA type are further engineered to express one or more selected antigens for therapeutic or protective immunization, or to suppress an unwanted immune response. The engineered cell lines can be propagated in cell culture to generate large numbers of cells and the cells can be stored, e.g. in liquid nitrogen, for convenient recovery for therapeutic use, or for use as target cells for assays of antigen-specific CTLs in a subject.

Various publications are cited herein that are hereby incorporated by reference in their entirety.

As will be apparent to those skilled in the art in which the invention is addressed, the present invention may be embodied in forms other than those specifically disclosed without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

I claim:

1. A cell of heterologous or xenogeneic origin that is not a professional antigen presenting cell, wherein said cell is engineered to express at least one ABC transporter protein and at least one costimulation molecule to function as an antigen presenting cell.

2. The cell of claim 1, wherein said protein is TAP 1 and/or TAP 2 protein.

3. A cell of heterologous or xenogeneic origin that is not a professional antigen presenting cell, wherein said cell is engineered to express at least one chemokine molecule and at least one costimulation molecule to function as an antigen presenting cell.

4. The cell of claim 3 wherein said chemokine molecule is selected from the group consisting of MCP-1 and RANTES.

5. A cell of heterologous or xenogeneic origin that is not a professional antigen presenting cell, wherein said cell is engineered to express at least one costimulation molecule to function as an antigen presenting cell, and wherein said costimulation molecule is selected from the group consisting of B7-1, B7-2, and B7-3.

6. A cell of heterologous or xenogeneic origin that is not a professional antigen presenting cell, wherein said cell is engineered to express an immunoregulatory molecule and at least one costimulation molecule to function as an antigen presenting cell.

7. The cell of claim 6, wherein said immunoregulatory molecule is a lymphokine selected from the group consisting of interferons, interleukins and tumor necrosis factors.

8. The cell of claim 5, wherein said cell is further engineered to express HLA class I and class II molecules of different antigen specificity than endogenous HLA molecules of said cell.

9. The cell of claim 5, further engineered to express at least one selected antigen from the group consisting of cancer and infectious agent antigens.

10. A cell that is not a professional antigen presenting cell, wherein said cell is engineered to present a selected antigen to T cells and to suppress T cell activation by the selected antigen, and wherein said cell expresses at least one ABC transporter protein and at least one chemokine.

11. A cell that is not a professional antigen presenting cell, wherein said cell is engineered to present a selected antigen to T cells and to suppress T cell activation by the selected antigen, and to express HLA class I and class II molecules of different antigen specificity than endogenous HLA molecules of said cell.

12. A cell of heterologous or xenogeneic origin that is not a professional antigen presenting cell, wherein said cell is engineered to express at least one costimulation molecule to function as an antigen presenting cell, and wherein said costimulation molecule is selected from the group consisting of 4.1 BB ligand, LFA-3, CD72, heat-stable and CD40 molecules.

13. A human cell line that is not a professional antigen presenting cell line and that originally expressed at least one endogenous human HLA molecule of an endogenous antigen specificity, said cell line engineered to express human HLA class I and class II molecules of different antigen specificity than the endogenous HLA molecules of said cell line.

14. The cell line of claim 13, engineered to express at least one costimulation molecule.

15. A cell line that is not a professional antigen presenting cell line, wherein said cell line is engineered to express human HLA class I and class II molecules of different antigen specificity than the endogenous HLA molecules of said cell line and at least one costimulation molecule selected from the group consisting of B7-1, B7-2, and B7-3.

16. A cell line that lacks expression of costimulation molecules for T cell activation and that is not a professional antigen presenting cell line, wherein said cell line is engineered to express human HLA class I and class II molecules of different antigen specificity than the endoegnous HLA molecules of said cell line.

17. A cell line that is not a professional antigen presenting cell line, wherein said cell line is engineered to express human HLA class I and class II molecules of different antigen specificity than the endogenous HLA molecules of said cell line and at least one chemokine molecule.

18. The cell line of claim 17, wherein said chemokine molecule is selected from the group consisting of MCP-1 and RANTES.

19. A cell line that is not a professional antigen presenting cell line, wherein said cell line is engineered to express human HLA class I and class II molecules of different antigen specificity than the endogenous HLA molecules of said cell line and at least one ABC transporter protein.

20. The cell line of claim 19, wherein said ABC transporter protein is selected from the group consisting of TAP-1 and TAP-2 proteins.

21. A cell line that is not a professional antigen presenting cell line, wherein said cell line is engineered to express human HLA class I and class II molecules of different antigen specificity than the endogenous HLA molecules of said cell line; and at least one immunoregulatory molecule.

22. The cell line of claim 21, wherein said immunoregulatory molecule is a lymphokine selected from the group consisting of interferons, interleukins and tumor necrosis factors.

23. The cell line of claim 13, wherein said cell line is further engineered to express one or more selected antigens selected from the group consisting of an infectious agent or cancer antigen.

24. The cell line of claim 16, wherein said cell line is further engineered to express one or more selected antigens from the group consisting of autoantigens, transplantation antigens and allergens.

25. A cell line that is not a professional antigen presenting cell line, wherein said cell line is engineered to express human HLA class I and class II molecules of different antigen specificity than the endogenous HLA molecules of said cell line and at least one costimulation molecule selected from the group consisting of 4.1 BB ligand, LFA-3, CD72, heat-stable and CD40 molecules.

26. A plurality of engineered antigen presenting cell lines according to claim 13, each cell line engineered to express HLA class I and class II molecules of a single specificity and different cell lines expressing different HLA specificities corresponding to those of a range of human hosts.

* * * * *